(12) United States Patent
White et al.

(10) Patent No.: US 11,759,116 B2
(45) Date of Patent: Sep. 19, 2023

(54) DETERMINING BLOOD FLOW USING LASER SPECKLE IMAGING

(71) Applicant: Covidien AG, Neuhausen Am Rheinfall (CH)

(72) Inventors: Sean Michael White, Santa Ana, CA (US); Bruce Yee Yang, Irvine, CA (US); Tyler Bywaters Rice, Santa Ana, CA (US)

(73) Assignee: Covidien AG, Neuhausen Am Rheinfall (CH)

( * ) Notice: Subject to any disclaimer, the term of this patent is extended or adjusted under 35 U.S.C. 154(b) by 169 days.

(21) Appl. No.: 17/091,803

(22) Filed: Nov. 6, 2020

(65) Prior Publication Data

US 2021/0177283 A1    Jun. 17, 2021

Related U.S. Application Data

(60) Provisional application No. 62/948,506, filed on Dec. 16, 2019.

(51) Int. Cl.
*A61B 5/026* (2006.01)
*A61B 5/022* (2006.01)
*A61B 5/0295* (2006.01)
*A61B 5/00* (2006.01)

(52) U.S. Cl.
CPC .......... *A61B 5/0261* (2013.01); *A61B 5/0295* (2013.01); *A61B 5/02241* (2013.01); *A61B 5/7235* (2013.01); *A61B 5/743* (2013.01)

(58) Field of Classification Search
CPC . A61B 5/0261; A61B 5/02241; A61B 5/0295; A61B 5/7235; A61B 5/743; A61B 5/02007; A61B 5/6826; A61B 5/6829; A61B 5/7239; A61B 5/7246; A61B 5/7257; A61B 5/726
See application file for complete search history.

(56) References Cited

U.S. PATENT DOCUMENTS

2008/0188733 A1* 8/2008 Al-Ali ................. A61B 5/6843
                                                600/509
2011/0013002 A1* 1/2011 Thompson ............. A61B 5/445
                                                382/128

(Continued)

OTHER PUBLICATIONS

Response to Extended Search Report dated May 14, 2021, from counterpart European Application No. 20213456.5, filed Dec. 9, 2021, 12 pp.

(Continued)

*Primary Examiner* — Eric F Winakur
*Assistant Examiner* — Abid A Mustansir
(74) *Attorney, Agent, or Firm* — Shumaker & Sieffert, P.A.

(57) ABSTRACT

In some examples, a system includes processing circuitry configured to generate a laser speckle contrast signal based on a received signal indicative of detected light, wherein the detected light is scatted by tissue from a coherent light source. The processing circuitry may also determine, from the laser speckle contrast signal, a flow value and determine, from the laser speckle contrast signal, a waveform metric. Based on the flow value and the waveform metric, the processing circuitry may determine a blood flow metric for the tissue and output a representation of the blood flow metric.

20 Claims, 6 Drawing Sheets

(56) References Cited

U.S. PATENT DOCUMENTS

| | | | |
|---|---|---|---|
| 2012/0277559 A1* | 11/2012 | Kohl-Bareis | A61B 5/0261 600/479 |
| 2013/0204112 A1* | 8/2013 | White | A61B 5/0261 600/407 |
| 2018/0153420 A1* | 6/2018 | Fine | A61B 5/02416 |
| 2018/0214025 A1* | 8/2018 | Homyk | A61B 5/0082 |
| 2018/0296168 A1 | 10/2018 | Rice et al. | |

OTHER PUBLICATIONS

Extended Search Report from counterpart European Application No. 20213456.5, dated May 14, 2021, 9 pp.

Luft et al., "Ocular Blood Flow Measurements in Healthy White Subjects Using Laser Speckle Flowgraphy," PLOS One, vol. 11, No. 12, DOI:10.I371,/journal.pone.0168190, Dec. 13, 2016, 17 pp.

Vas et al., "Laser speckle contrast analysis for pulse waveform extraction," Progress in Biomedical Optics and Imaging, SPIE—International Society for Optical Engineering, vol. 9540, DOI:10.LLIT/12.21,83293, Jul. 17, 2015, 7 pp.

Humeau-Heurtier et al., "Relevance of Laser Doppler and Laser Speckle Techniques for Assessing Vascular Function: State of the Art and Future Trends", IEEE Transactions on Biomedical Engineering, vol. 60, No. 3, Mar. 2013, pp. 659-666.

Belcaro et al., "Evaluation of Skin Blood Flow and Venoarteriolar Response in Patients with Diabetes and Peripheral Vascular Disease by Laser Doppler Flowmetry", The Journal of Vascular Diseases, Nov. 1989, pp. 953-957.

Razavi et al., "A Real-Time Blood Flow Measurement Device for Patients with Peripheral Artery Disease", J Vasc Interv Radiol, Mar. 2021, pp. 453-458.

\* cited by examiner

DETERMINING BLOOD FLOW USING LASER SPECKLE IMAGING

This application claims the benefit of U.S. Provisional Patent Application No. 62/948,506, filed on Dec. 16, 2019 and entitled "Algorithms for the Analysis of Transmission Laser Speckle Imaging Information," the entire contents of which are incorporated herein by reference.

TECHNICAL FIELD

This disclosure relates to blood flow monitoring.

BACKGROUND

Various technologies can be used to monitor aspects of blood flow. For example, photoplethysmography (PPG) is an optical technique for assessing blood volume changes in the arteries during the cardiac cycle. Following each systolic and diastolic phase of the heart, the arteries are thought to undergo subtle volumetric expansion and contraction, respectively, which changes the light absorption signal measured by PPG. In this way, PPG can provide a "waveform" for the cardiac cycle, which can be used to assess vitals of a subject, such as heart rate and oxygen saturation. As another example, Laser Speckle Imaging (LSI) is an optical technology for measuring blood flow.

SUMMARY

This disclosure describes devices, systems, and techniques for determining a blood flow metric using Laser Speckle Imaging (LSI). A system can generate a laser speckle imaging signal that is representative of blood flow within a tissue region of a patient, such as a digit (e.g., a finger or toe) or limb of the patient. The laser speckle imaging signal can change with pulsatile flow during a cardiac cycle of the patient, leading to a blood flow waveform over time. In some examples, the system is configured to analyze separate components of one or more waveforms of the laser speckle imaging signal, such as flow value and waveform shape, to determine a blood flow metric representative of the blood flow state of the tissue. The system can output the blood flow metric and/or a related diagnostic metric for use by another device and/or for display to a user.

In one example, a system includes processing circuitry configured to: generate a laser speckle contrast signal based on a received signal indicative of the detected light, the detected light scattered by tissue of a subject and from a coherent light source; determine, from the laser speckle contrast signal, a flow value; determine, from the laser speckle contrast signal, a waveform metric; determine, based on the flow value and the waveform metric, a blood flow metric for the tissue; and output a representation of the blood flow metric In another example, a method includes generating, by processing circuitry, a laser speckle contrast signal based on a received signal indicative of the detected light, the detected light scattered by tissue of a subject and from a coherent light source; determining, by the processing circuitry and from the laser speckle contrast signal, a flow value; determining, by the processing circuitry and from the laser speckle contrast signal, a waveform metric; determining, by the processing circuitry and based on the flow value and the waveform metric, a blood flow metric for the tissue; and outputting, by the processing circuitry, a representation of the blood flow metric.

In another example, a non-transitory computer-readable medium comprising instructions that, when executed, causes processing circuitry to: generate a laser speckle contrast signal based on a received signal indicative of the detected light, the detected light scattered by tissue of a subject and from a coherent light source; determine, from the laser speckle contrast signal, a flow value; determine, from the laser speckle contrast signal, a waveform metric; determine, based on the flow value and the waveform metric, a blood flow metric for the tissue; and output a representation of the blood flow metric The details of one or more examples are set forth in the accompanying drawings and the description below. Other features, objects, and advantages will be apparent from the description and drawings, and from the claims.

DETAILED DESCRIPTION

Figure 1:
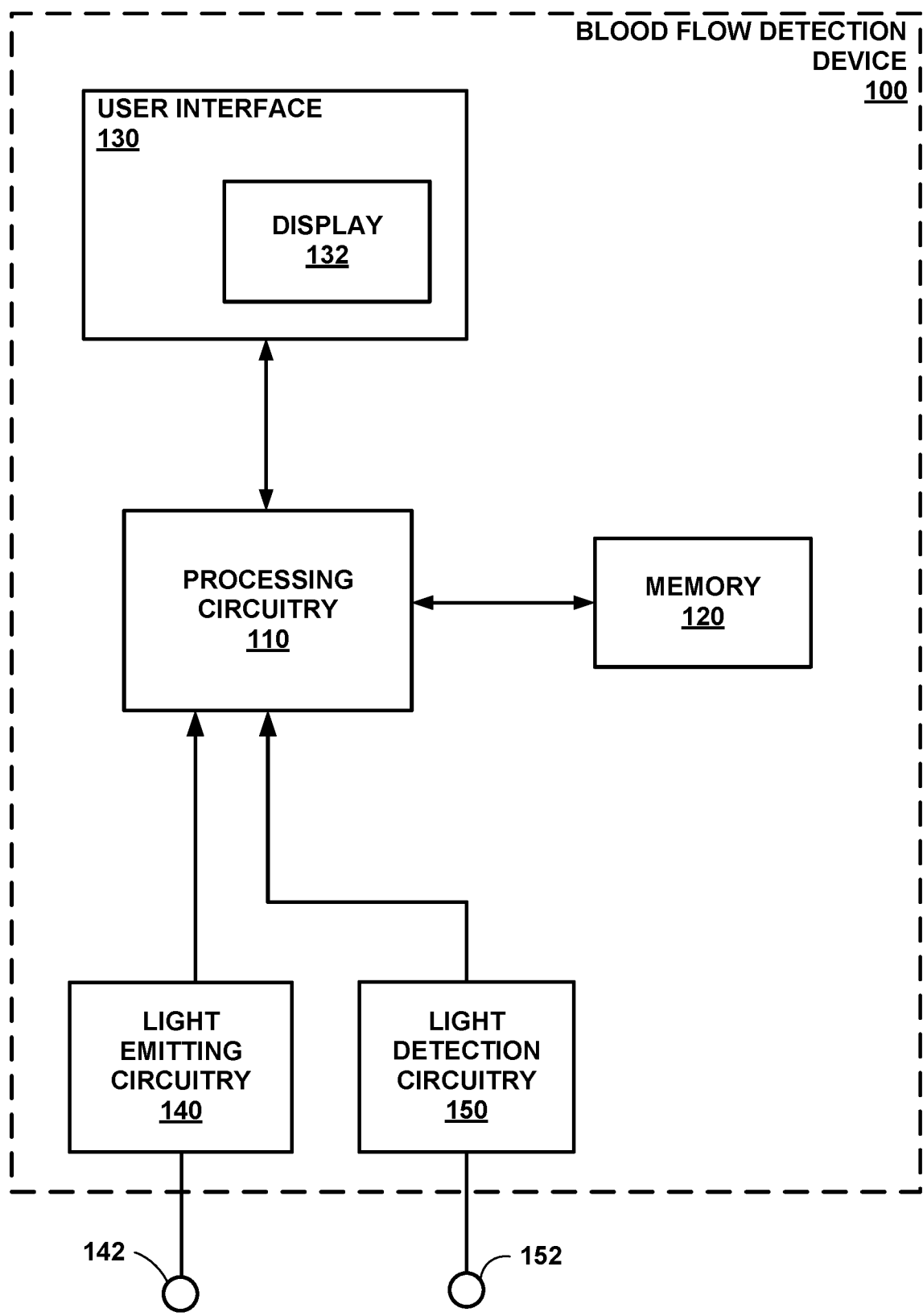
FIG. 1 is a conceptual block diagram illustrating an example blood flow detection device.

This disclosure describes devices, systems, and techniques for determining blood flow states of a subject using multiple aspects of a laser speckle imaging waveform. Photoplethysmography (PPG) is an optical technique for assessing blood volume changes in the arteries during the cardiac cycle. Following each systolic and diastolic phase of the heart, the arteries are thought to undergo subtle volumetric expansion and contraction, respectively, which changes the light absorption signal measured by PPG. In this way, PPG can provide a "waveform" for the cardiac cycle, which can be used to assess vitals of a subject, such as heart rate and oxygen saturation. PPG is a useful technology, but can have some shortcomings due to its reliance on solely volumetric changes. Some circumstances that can cause errors in a PPG signal include one or more of low blood perfusion, low cardiac output, stiff/hardened arteries, vasoconstriction, hypoperfusion, vascular disease, arterial occlusion, and the like or combinations thereof.

Laser Speckle Imaging (LSI) is an optical technology for measuring blood flow, and can also provide a cardiac waveform for vital signs monitoring. LSI varies from PPG in several key ways, and has the capability of improving medical diagnostics and monitoring beyond what may be possible with PPG. Unlike PPG, LSI is sensitive to the motion of light scatterers such as erythrocytes, rather than changes in light absorption. Processing of LSI data thus quantifies the movement of blood and not solely absorption changes associated with volumetric fluctuations in blood within the tissue of interest as performed by PPG. For at least this reason, LSI does not suffer from many of the shortcomings of PPG, and can potentially provide reliable measurements under all states of perfusion and vascular tone of a subject. Further, LSI measurements intrinsically entail the collection of PPG data since PPG information can be derived from LSI data, but LSI information cannot be attained from a setup designed specifically for PPG measurements. Thus, a LSI device may provide more robust patient data than a PPG sensor alone.

In this manner, data attained through PPG and LSI can appear similar to some degree with regards to information that can be extracted, such as heart rate. However, the fact that LSI measures a distinct parameter different from PPG potentially enables more accurate diagnosis and monitoring of physiological states of a subject where blood flow measurement could prove to be advantageous. As such, a system that leverages LSI to quantify blood flow and hemodynamics can provide valuable information regarding many medical conditions and situations, from disease diagnostics to surgical status to training and rehabilitation.

The devices, systems, and techniques of this disclosure may enable the determination of blood flow metrics for tissue of a subject (also referred to as a patient herein) from multiple characteristics of a LSI waveform. Laser speckle analysis performed using transmitted coherent light presents distinct advantage over coherent interference techniques using reflected light, such as laser Doppler, or reflection-based LSI. When LSI is performed on a digit (e.g., a finger or toe) of a subject, the detected light is captured on the opposite side of the digit as the coherent illumination, and, as a result, the light interacts with the entire tissue volume (e.g., digit volume). This may provide an improved metric of overall blood flow and stronger signal (e.g., greater amplitude and/or stronger signal to noise ratio) compared to using reflected light. This is contrasted with reflectance techniques which generally interrogate the first 1-2 millimeters (mm) of tissue, and thus are sensitive only to skin perfusion. The largely diffuse nature of transmitted light also ensures measurement repeatability, as each value is an average of the entire finger (or other digit) volume and less susceptible to variation based on of the specific location of the illumination source and detection element. Alternatively, reflectance techniques analyzed light that is significantly less diffuse, and significant variability in measured blood flow speed has been demonstrated depending on where the probe has been placed. This variability reduces clinical utility.

In examples described herein, processing circuitry of a system is configured to obtain a raw signal generated by a light detector that detects light scattered through tissue of a subject from a light source (e.g., a coherent light source). The processing circuitry may then generate a LSI signal from this raw signal to provide a representation of blood flow over time for the tissue. For example, the LSI signal may include a wave form that at least partially reflect blood flow changes due to the pulsatile nature of the cardiac cycle (or lack thereof). The processing circuitry may determine multiple characteristics of the LSI signal, such as a flow (e.g., blood flow) and waveform metric of one or more waveforms of the LSI signal. For example, the flow may be the measured flow (e.g., a flow value which can be the mean or median flow determined over a period of time, and may be represented by the amplitude of the waveform) of some or all of one or more waveforms. The waveform metric may characterize the shape of one or more waveforms, such as one or more of how many peaks reside within one waveform representative of a single cardiac cycle, one or more slopes of the waveform, a power spectrum of the frequencies of the waveform, a shape identified by one of a plurality of waveform templates, or any other such characteristics or combinations thereof.

Based on multiple characteristics of the waveform, the processing circuitry may determine a blood flow metric. Since this blood flow metric takes into account characteristics of the waveform other than just the overall flow rate, the blood flow metric may be indicative of different blood flow states of the tissue that may differentiate between healthy and compromised blood flow. This blood flow metric may provide more accurate information regarding compromised circulation for the patient in at least that tissue sampled. The system may transmit the blood flow metric to another device as feedback for a therapy or procedure, or the system may display the blood flow metric for use by a clinician when diagnosing or treating the patient. In some examples, the system may provide a diagnostic metric indicative of whether or not the patient is likely to have a blood flow disorder, such as peripheral vascular disease (PVD), that is affecting the sampled tissue.

Processing circuitry implementing the devices, systems, and techniques of this disclosure may present advantages over other systems. For example, LSI signals can be reflective of light passing through an entire volume of tissue instead of just surface tissue for a reflected signal. This increased volume may provide an improved overall view of blood flow for the tissue, digit, and patient as a whole. Moreover, determining the blood flow metric using the waveform metric of the LSI signal enables blood flow metric to be sensitive to diseased or damaged vasculature or other issues that manifest as improper blood flow profiles. For example, the blood flow metric based on LSI signals may differentiate between normal vasoconstriction (e.g., from the patient being merely cold) and pathologically diminished tissue perfusion when both conditions result in reduced blood flow, but with distinct blood flow waveforms. For example, a healthy patient who is vasoconstricted may exhibit a multi-phasic waveform with reduced average blood flow rate, whereas a patient with peripheral artery disease may exhibit a dampened monophasic waveform with similarly reduced average blood flow rate. In this manner, the blood flow metric generated as described herein may enable more precise detection of abnormal issues with circulation or other conditions of the patient using a non-invasive technique.

FIG. 1 is a conceptual block diagram illustrating an example blood flow detection device 100. The blood flow detection device 100 includes processing circuitry 110, a memory 120, a user interface 130 including a display 132, light emitting circuitry 140, a light source 142, light detection circuitry 150, and a light sensor 152. In some examples, the blood flow detection device 100 is configured to determine and display the blood flow metric of a patient or tissue of a patient, e.g., for diagnosis, during a medical procedure or for more long-term monitoring. A clinician may receive information regarding the blood flow metric of a patient via the display 132 (or another output, such as audio circuitry configured to generate a sound) and diagnose or adjust treatment or therapy to the patient based on the blood flow metric.

The processing circuitry 110 as well as other processors, processing circuitry, controllers, control circuitry, and the like, described herein, may include one or more processors. The processing circuitry 110 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, the processing circuitry 110 may include multiple components, such as any combination of one or more microprocessors, one or more DSPs, one or more ASICs, or one or more FPGAs, as well as other discrete or integrated logic circuitry, and/or analog circuitry.

The memory 120 may be configured to store data related to the blood flow metric, such as raw signals from the light detection circuitry 150, LSI signals, or other information, for example. In some examples, the memory 120 may be configured to store information related to other sensed information from other sensors or devices, which may be displayed with the blood flow metric in some examples. The memory 120 may also be configured to store information, such as instructions for determining the blood flow metric, diagnostic metrics, characteristics of the LSI signal (e.g., flow and waveform metrics), controlling the light emitting circuitry 140 and the light detection circuitry 150, the controlling the user interface 130, or any other such information related to the operation of the blood flow detection device 100.

In some examples, the memory 120 stores program instructions, which may include one or more program modules, which are executable by the processing circuitry 110. When executed by the processing circuitry 110, such program instructions cause the processing circuitry 110 to provide the functionality ascribed to it herein. The program instructions may be embodied in software, firmware, and/or RAMware. The memory 120 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

The user interface 130 and/or the display 132 may be configured to present information to a user (e.g., a clinician). For example, the user interface 130 and/or the display 132 may be configured to present a graphical user interface to a user, where each graphical user interface may include indications of values of one or more physiological parameters of a subject. For example, the processing circuitry 110 may be configured to present blood pressure values, physiological parameter values, and indications of the blood flow metric over time, or disease status of a patient via the display 132. In some examples, if the processing circuitry 110 determines that the blood flow metric of the patient is indicative of an impaired condition, then the processing circuitry 110 may present a notification (e.g., an alert) indicating the impaired blood flow of the patient status via the display 132.

The user interface 130 and/or the display 132 may include a monitor, cathode ray tube display, a flat panel display such as a liquid crystal (LCD) display, a plasma display, or a light emitting diode (LED) display, personal digital assistant, mobile phone, tablet computer, laptop computer, any other suitable display device, or any combination thereof. The user interface 130 may also include means for projecting audio to a user, such as audio generation circuitry and speaker(s). The processing circuitry 110 may be configured to present, via the user interface 130, a visual, audible, or somatosensory notification (e.g., an alarm signal) indicative of the patient's blood flow metric. The user interface 130 may include or be part of any suitable device for conveying such information, including a computer workstation, a server, a desktop, a notebook, a laptop, a handheld computer, a mobile device, or the like. In some examples, the processing circuitry 110 and the user interface 130 may be part of the same device or supported within one housing (e.g., a computer or monitor). In other examples, a user interface separate from the blood flow detection device 100 can be configured to present information regarding blood flow metrics to a user, where such information may be provided to the user interface via the processing circuitry 110.

The light emitting circuitry 140 is configured to control light source 142 to generate light. For example, the light source 142 may include a coherent light source (e.g., a laser light source) emitting light having substantially the same frequency. Light sensor 152 includes one or more light sensitive structures configured to convert light energy into electric signals (e.g., a photoelectric device such as a charge-coupled device (CCD or some other sensor). The light detection circuitry 150 may power and receive the electrical signals from the light sensor 152. The light detection circuitry 150 may then generate a raw signal representative of the light detected by the light sensor 152. In some examples, the light detection circuitry 150 may perform initial processing and/or analog to digital conversion of the electrical signals from the light sensor 152 to generate the raw signal that is usable by processing circuitry 110 to generate the LSI signal. In other examples, light detection circuitry 150 may include processing circuitry configured to generate the LSI signal.

In operation, the light source 142 and the light sensor 152 are each placed on different locations on parts of a body of a patient such that the light sensor 152 can detect light scattered from the light emitted by the light source 142. For example, the light source 142 and the light sensor 152 may be positioned on opposite surfaces of a digit, such as a finger or toe. The light source 142 and the light sensor 152 may be physically separate from each other and separately placed on the patient. As another example, the light source 142 and the light sensor 152 are part of the same sensor or supported by a single sensor housing. For example, the light source 142 and the light sensor 152 may be part of an integrated sensor system configured to non-invasively measure blood flow of the tissue between the light source 142 and the light sensor 152.

While an example blood flow detection device 100 is shown in FIG. 1, the components illustrated in FIG. 1 are not intended to be limiting. Additional or alternative components and/or implementations may be used in other examples.

Processing circuitry 110 is configured to generate a LSI signal using the raw signal from light detection circuitry 150, where the LSI system provides laser speckle contrast measurements over time. LSI is an imaging methodology used to create image-based representations of blood flow in tissues of interest. LSI illuminates a part of a patient's body, e.g., a finger or toe, using coherent light. The presence and movement of blood within the illuminated body part interacts with the light moving through the tissue. Thus, coherent laser light is scattered within samples of interest. These scattering events lead to a difference in path length among photons. The result is a speckle pattern that is typically imaged using the light sensor 152 (e.g., a light detector), such as a camera with a finite exposure time. If the scattering objects (such as blood cells) are in motion, then the speckle pattern fluctuates in time and blurs during the camera exposure. The amount of blurring is related to flow and quantified using a parameter called the speckle contrast.

Various features of alteration can be used to extract information about the presence and flow of blood. Such features can include, for example, changes in detected light intensity and contrast within the observed light pattern, both of which are correlated with the movement of red blood cells. Analysis of changes in intensity and contrast within the observed light pattern over time then provides dynamic and quantitative feedback about alterations in a patient's peripheral blood flow and tissue perfusion, from which informed inferences may be made with respect to the physical state of a patient. Because it has been shown that this information can be acquired under circumstances where pulse oximeters (which can be used for analysis of patient hemodynamics) no longer function adequately, LSI provides information to clinicians that can be useful to the proactive treatment of critically ill patients.

In some examples, the locations of the coherent light source 142 and the light sensor 152 are coupled to the movement of the tissue sample. As such, patient movement causes the light sensor 152 and the coherent light source 142 to similarly move. Accordingly, the field of view of the tissue sample does not change upon movement of the tissue sample. The coupling of the light sensor, coherent light source, and tissue sample may be facilitated by shortening the distance between the light sensor 152 and coherent light source 142. The distance between the light sensor 152 and the coherent light source 142 may be shortened by reducing the field of view of the light sensor 152 and forgoing the formation of a focused image, thereby eliminating the need for a focal length. In other examples, an unfocused image may be preferred to be received by the light sensor 152. In some examples, the coherent light source 142 and the light sensor 152 are included in a compact enclosure, such as a clam shell. The clam shell may be configured to accommodate a tissue sample of a patient, such as a finger or toe.

In some examples, the light source 142 is configured to emit coherent light via an optical fiber coupled with a laser source. In these examples, the optical fiber may emit a portion of the coherent light emitted by the coherent light source 142. The location of the coherent light source 142 can be coupled to patient movement by fixing the location of the coherent light source 142 and/or the optical fiber with respect to the tissue sample. As used herein, "coherent light source" can include coherent light emitted via an optical fiber and/or the coherent light source itself.

In some examples, the device 100 does not require the formation of a focused image on the light sensor 152 of the light sensor. Thus, some examples of the light source 142 and/or the light sensor 152 may forgo lenses, thereby reducing the cost and size compared to other LSI systems. In addition, other LSI systems require a light sensor with image-forming optics, whereas some examples devices 100 described herein may use a cheaper light sensor without image-forming optics, such as a photodiode.

In some examples, the light sensor 152 may include an opaque sheet with an aperture near the light sensor 152. The opaque sheet increases the speckle size incident on the light sensor, and thus obviates an issue of under-sampling traditionally associated with unfocused images and small speckle sizes. Additionally, in some examples, the processing circuitry 110 determines perfusion using values using all the pixels in an image, instead of small sliding windows. By doing so, artifacts from streaking images are eliminated. In addition, the fact that the direction of perfusion in fingertips is random also helps to remove artifacts.

As described generally herein, the light source 142 and the light sensor 152 are used in a transmission geometry. In a transmission geometry, the light source 142 and the light sensor 152 are positioned on opposite sides of a tissue of interest. Thus, the light sensor is configured to receive transmitted light that travels through the entire thickness of the tissue. As mentioned, because blood is very highly forward scattering, the usage of transmitted light rather than backscattered light provides a higher signal to noise ratio than a reflection geometry. In addition, transmission geometry enables signal acquisition from all of the blood vessels or the majority of blood vessels within the tissue of interest.

Furthermore, transmission geometry enables the light source 142 to be placed in close proximity to the sample of interest. In some examples, the light source 142 contacts the surface of the sample of interest. In LSI, the light exits from the field of view of the tissue in order to capture an accurate image. Otherwise, the light may obstruct the region of tissue being imaged. However, because the light is transmitted through the sample in a transmission geometry in some examples, rather than reflected back, transmission geometry enables the light source 142 to be placed in close proximity to the sample (region of tissue being imaged).

The light source 142 may be configured to transilluminate the entire thickness of a digit. Similarly, the light sensor 152 can be configured to receive transmission light after it travels through the entire thickness of the digit. In some examples, the light source 142 may be chosen to maximize transmission of the light through the tissue of interest. For example, the light source 142 may be a laser having a wavelength ranging from 300 nm to 1100 nm. The light source 142 may further be chosen to maximize speckle contrast at the light sensor 152. The light source 142 may be a single-mode laser diode or a fiber coupled helium-neon laser according to some examples. In some examples, the light source 142 includes adjustable power output to provide an adequate signal at the light sensor 152. In some examples, the light sensor 152 may be a camera with or without image-forming optics, such as a charge-coupled device (CCD) camera or a complementary metal-oxide semiconductor (CMOS) camera. The light sensor 152 may also be a camera without image-forming optics, such as a photodiode.

In some examples, the device 100 can include one or more polarizers that are configured to convert light before the light reaches the light sensor 152 and after it transilluminates the digit of a patient. Placing the polarizer to convert light before the light enters the digit would not be as effective, because light entering scattering tissue such as the digit becomes depolarized as it is scattered. An optical filter may also be included in order to filter out light not coming from the light source 142.

Processing circuitry 110 may determine the blood flow (e.g., perfusion) within the tissue sample using the speckle pattern detected by the light sensor 152. For example, the light sensor 152 generates electrical signals representative of light intensity and the light detection circuitry 150 generates a raw signal that represents captured frames associated with different light intensity values detected. The light intensity values captured by the light sensor 152 are indicative of coherent light that was scattered by red blood cells as it transilluminated the digit. The coherent light transilluminating the digit renders an unfocused image, which is captured by the light sensor 152. The light sensor 152 is configured to adequately sample the speckle pattern despite the unfocused image. In some examples, speckle sizes are increased by an opaque sheet with an aperture which alters the numerical aperture of the light sensor 152.

Based on the light intensity values associated with the unfocused image as provided by the raw signal, the processing circuitry 110 may compute speckle contrast spatially, temporally, or spatio-temporally (a hybrid of spatial and temporal). To compute speckle contrast spatially, the processing circuitry 110 may utilize a group of pixels at different spatial locations within the same frame. To compute speckle contrast temporally, the processing circuitry 110 may utilize pixels from the same spatial location across a sequence of frames captured at different times. The processing circuitry 110 may also compute speckle using a spatio-temporal method, which is a hybrid of the temporal and spatial methods. In any case, the processing circuitry 110 may calculate the speckle contrast.

In some examples, the processing circuitry 110 is configured to determine the speckle contrast by at least using the following equation:

$$K=\sigma/\langle I \rangle, \quad (1)$$

where K is contrast, $\sigma$ is the standard deviation of a group of pixel values and $\langle I \rangle$ is the average of a group of pixel values.

Generally, acquisition of the LSI signal does not require a focused image (e.g., the light sensor 152 received an unfocused image. Therefore, the processing circuitry 110 may determine speckle contrast temporally from only one pixel location in some examples. Accordingly, the blood flow detection device 100 may use a photodiode as the light sensor 152 in some examples. Photodiodes are cheaper than cameras with image-forming optics. It is believed that in some cases, perfusion measurements acquired by utilizing only one pixel location may be comparable in accuracy to those acquired by utilizing multiple pixel locations. In addition, perfusion measurements acquired by utilizing pixels from an unfocused image are comparable in accuracy to those acquired by laser Doppler. In other examples, device 100 can utilize a focused image to generate the LSI signal and determine the blood flow metrics as described herein.

In some examples, in addition to or instead of the other techniques described herein, the processing circuitry 110 is configured to determine the speckle contrast using the standard deviation across the entire image generated by light sensor 152 and light detection circuitry 150. Doing so reduces or even eliminates the artifacts in the "streaking images" that may otherwise result from using an unfocused image. If the object being imaged is moved during the imaging, the out of focus speckle pattern may translate. These artifacts may propagate to the speckle contrast image, creating "streaking images." In-focus speckles do not translate, and thus the speckle contrast image does not exhibit the streaking images. The streaking in unfocused images may be eliminated by calculating the standard deviation across the entire image. In addition, streaking is eliminated because of the random direction of motion of blood perfusion.

After calculating the speckle contrast value K, the processing circuitry 110 can calculate perfusion as:

$$\text{Perfusion}=1/K^2 \quad (2)$$

Other factors may affect this computation, including camera exposure time, camera noise, optical absorption, and the presence of static scatterers.

Using equation (2), the processing circuitry 110 may determine a metric of perfusion based on the computed speckle contrast value. For example, the LSI signal may indicate the perfusion metric as it changes over time. Moreover, the processing circuitry 110 may analyze the LSI signal in order to determine several characteristics, such as a flow and waveform metric. The processing circuitry 110 then determines a blood flow metric from the flow and waveform metric, for example, which provides a more complete representation of how blood is being moved within the tissue of interest.

As described herein, the device 100 can include processing circuitry 110 configured to generate a laser speckle contrast signal based on a received signal indicative of the detected light from the light detection circuitry 150, where the detected light scatted by tissue from a coherent light source (e.g., the light source 140). The processing circuitry 110 can then determine, from the laser speckle contrast signal, a flow value and determine, from the laser speckle contrast signal, a waveform metric. The processing circuitry 110 can then also determine, based on the flow value and the waveform metric, a blood flow metric for the tissue. The processing circuitry 110 then outputs a representation of the blood flow metric, such as a representation that is presented by display 132 or another output mechanism, such as audio generating circuitry.

The waveform metric may be representative of one or more waveforms included in the LSI signal. In one example, one waveform is the pulsatile signal corresponding to one cardiac cycle, for example. Since the manner in which blood pulses through the vasculature can be reflective of certain conditions, this waveform may be indicative of such conditions. In some examples, the processing circuitry 100 may be configured to determine the waveform metric by at least determining the waveform metric based on the laser speckle contrast signal comprising one of a triphasic waveform, a biphasic waveform, a monophasic waveform, or a non-phasic waveform. In other words, the number of phases, or peaks, within one waveform may be indicative of how normal the blood flow is. Generally, more phases, or peaks, within the waveform is indicative of normal pulsatile flow. In addition, the system may determine the amplitude of one or more peaks (e.g., the amplitude with respect to baseline or troughs between peaks) and determine the waveform metric based at least in part on the determined amplitude. For example, higher amplitudes may correspond to higher waveform metrics.

In another example, the processing circuitry 110 is configured to determine the waveform metric by at least comparing a waveform shape of the laser speckle contrast signal to a plurality of different waveform templates and selecting the waveform metric corresponding to one waveform template of the plurality of different waveform templates that best fits the waveform shape. For example, the memory 120 may store a plurality of waveform templates corresponding to different degraded levels of flow, and the processing circuitry 110 may select the waveform template, and corresponding numerical metric, that best fits the detected waveform. The processing circuitry 110 may determine the flow of the waveform, such as the total flow of the waveform or flow from a portion of the waveform (e.g., the area under the curve of the blood flow rate over time for the waveform) or some other measure of blood movement for the waveform.

In some examples, the processing circuitry 110 can perform waveform decomposition (e.g., using one or more waveforms from the LSI signal) using any one or more of different approaches to classify the waveforms as a waveform metric. Exemplary classification techniques for determining the waveform metric may include one or more of a waveform quality metric (e.g., based on template matching), diastolic flow values, systolic flow values, peak to trough amplitude (e.g., between adjacent peak and troughs or between systolic and diastolic portions), mean flow, standard deviation of flow, the slope (e.g., the delta or change) of flow (e.g., a maximum value of a derivative of the LSI signal), the ratio of the maximal slope of the LSI signal (e.g., a systolic-ejection slope) to one of a systolic flow, a diastolic flow, or a mean flow, and/or a frequency domain value. Examiner frequency domain values may include one or more coefficients of Fourier or Wavelet transform. The processing circuitry 110 may determine the waveform metric, or blood flow metric, based on any one or combination of these values. In one example, the processing circuitry 110 may determine the waveform metric as a ratio of the maximal slope (e.g., the maximum derivative of the LSI signal) of one or more waveforms to the systolic flow value for the one or more waveforms.

The processing circuitry 110 may then determine the flood flow metric based on several characteristics from the LSI signal, such as the flow value and the waveform metric. In some examples, the processing circuitry 110 is configured to determine the blood flow metric based on a total score of the flow value and the waveform metric. Lower flow values and lower waveform metrics may be indicative of reduced blood flow and vascular function, so higher total scores of the flow and waveform metric may represent better overall vascular function and better perfusion. In some examples, the processing circuitry 110 may determine that the blood flow metric is insufficient if the total score is below a predetermined threshold. In other examples, the processing circuitry 110 is configured to determine the blood flow metric from a lookup table defining a relationship between the flow value and the waveform metric. For example, the lookup table may identify combinations of the flow value and the waveform metric that result in a specific blood flow metric. As another example, the processing circuitry 110 may determine the blood flow metric according to a formula that may or may not weight the flow value and/or the waveform metric.

In some examples, the processing circuitry 110 may determine both the flow value and the waveform metric from the same one waveform or same multiple waveforms. For example, the processing circuitry 110 may be configured to determine the flow value by at least determining an average flow of a plurality of waveforms of the laser speckle contrast signal and determine the waveform metric by at least determining an average waveform metric of the same plurality of waveforms of the laser speckle contrast signal. Alternatively, the processing circuitry 110 can determine the flow value and waveform metric from different waveforms or at least partially different sets of waveforms.

The blood flow metric may be representative of the state of perfusion and state of vascular function for the patient. In some examples, the processing circuitry 110 may determine a diagnostic metric for one or more conditions based on the blood flow metric and/or a change in the blood flow metric change over time. For example, the processing circuitry 110 may be configured to determine a peripheral vascular disease (PVD) metric based on the blood flow metric for the tissue, where the PVD metric indicates a quantitative or qualitative indication of a peripheral vascular disease state of the patient. The processing circuitry 110 can control the user interface 130 and/or display 132 to present the representation of the blood flow metric and/or a diagnostic metric. These metrics may be displayed as a single value, a graph of the metrics over time, or any other graphical, numerical, or textual representation. User interface 130 may present these metrics in real-time or nearly in real-time (e.g., with less than one second delays), via display 132.

Figure 2:
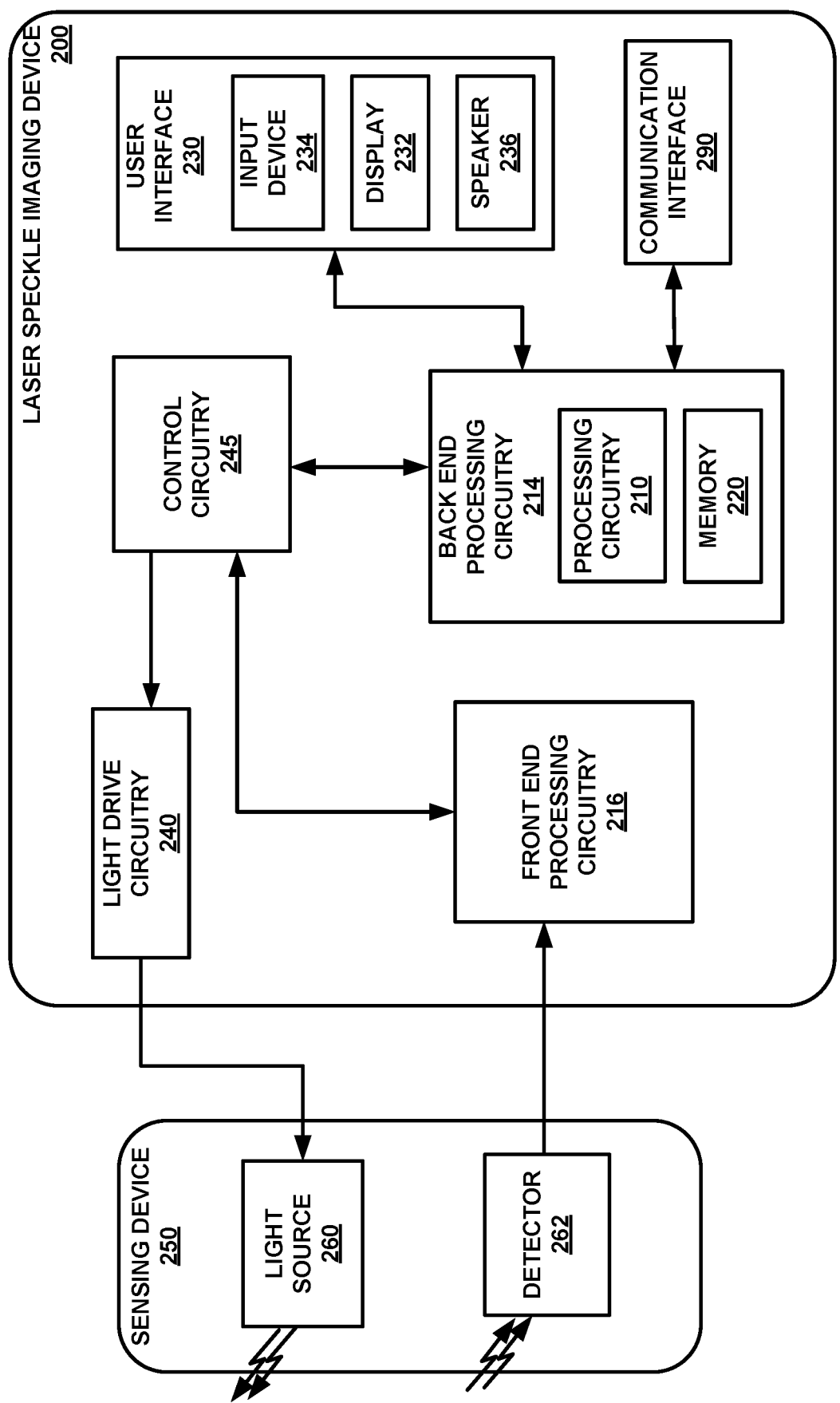
FIG. 2 is a conceptual block diagram illustrating an example blood flow detection device configured to monitor a blood flow state of at least a portion of a patient.

FIG. 2 is a conceptual block diagram illustrating an example laser speckle imaging (LSI) device 200 configured to monitor a blood flow state of at least a portion of a patient. In the example shown in FIG. 2, the LSI device 200 is coupled to a sensing device 250 and may be collectively referred to as a blood flow detection system, which generates and processes physiological signals of a subject. In some examples, the sensing device 250 and the LSI device 200 are part of a patient monitoring device. As shown in FIG. 2, the LSI device 200 includes the back-end processing circuitry 214, the user interface 230, the light drive circuitry 240, the front-end processing circuitry 216, the control circuitry 245, and the communication interface 290. The LSI device 200 is communicatively coupled to sensing device 250. The LSI device 200 is an example of the blood flow detection device 100 shown in FIG. 1. In some examples, the LSI device 200 may also include other physiological sensors.

In the example shown in FIG. 2, the sensing device 250 includes at least one light source 260 and at least one detector 262 (e.g., a light sensor). In some examples, the sensing device 250 may include more than two detectors. The light source 260 may be configured to emit photonic signals having coherent light (e.g., one wavelength of light) into a subject's tissue. For example, the light source 260 may include a laser source for emitting light into the tissue of a subject to generate detectable scattering of light. The light source 260 may include any number of light sources with any suitable characteristics. In examples in which an array of sensors is used in place of the sensing device 250, each sensing device may be configured to emit the same wavelength.

The detector 262 may be chosen to be specifically sensitive to the chosen targeted energy spectrum of the light source 260. In some examples, the detector 262 may be configured to detect the intensity of light that has been scattered by tissue, as described in FIG. 1. In some examples, an array of detectors may be used and each detector in the array may be configured to detect an intensity of a single wavelength. In operation, light may enter the detector 262 after passing through the subject's tissue, including skin, bone, and other tissue. The detector 262 may convert the intensity of the received light into an electrical signal. The light intensity may be directly related to the scattering of light from light scattering particles within the tissue that leads to the speckle contrast, as discussed with respect to FIG. 1.

After converting the received light to an electrical signal, the detector 262 may send the detection signals to the LSI device 200, which may process the detection signals and determine physiological parameters, such as the blood flow metric. In some examples, one or more of the detection signals are preprocessed by the sensing device 250 before being transmitted to the LSI device 200.

The control circuitry 245 may be coupled to the light drive circuitry 240, the front-end processing circuitry 216, and the back-end processing circuitry 214, and may be configured to control the operation of these components. In some examples, the control circuitry 245 is configured to provide timing control signals to coordinate their operation. For example, the light drive circuitry 240 may generate one or more light drive signals, which may be used to turn on and off the light source 260, based on the timing control signals provided by the control circuitry 245. The front-end processing circuitry 216 may use the timing control signals to operate synchronously with the light drive circuitry 240. For example, the front-end processing circuitry 216 may synchronize the operation of an analog-to-digital converter and a demultiplexer with the light drive signal based on the timing control signals. In addition, the back-end processing circuitry 214 may use the timing control signals to coordinate its operation with the front-end processing circuitry 216.

The light drive circuitry 240, as discussed above, may be configured to generate a light drive signal that is provided to the light source 260 of the sensing device 250. The light drive signal may, for example, control the intensity of the light source 260 and the timing of when the light source 260 is turned on and off. In some examples, the light drive circuitry 240 provides one or more light drive signals to the light source 260. In examples in which the light source 260 is configured to emit two or more wavelengths of light, the light drive signal may be configured to control the operation of each wavelength of light. The light drive signal may comprise a single signal or may comprise multiple signals (e.g., one signal for each wavelength of light).

The front-end processing circuitry 216 may perform any suitable analog conditioning of the detector signals. The conditioning performed may include any type of filtering (e.g., low pass, high pass, band pass, notch, or any other suitable filtering), amplifying, performing an operation on the received signal (e.g., taking a derivative, averaging), performing any other suitable signal conditioning (e.g., converting a current signal to a voltage signal), or any combination thereof. The conditioned analog signals may be processed by an analog-to-digital converter of circuitry 216, which may convert the conditioned analog signals into digital signals. The front-end processing circuitry 216 may operate on the analog or digital form of the detector signals to separate out different components of the signals. The front-end processing circuitry 216 may also perform any suitable digital conditioning of the detector signals, such as low pass, high pass, band pass, notch, averaging, or any other suitable filtering, amplifying, performing an operation on the signal, performing any other suitable digital conditioning, or any combination thereof. The front-end processing circuitry 216 may decrease the number of samples in the digital detector signals. In some examples, the front-end processing circuitry 216 may also remove dark or ambient contributions to the received signal.

The back-end processing circuitry 214 may include the processing circuitry 210 and the memory 220. The processing circuitry 210 may include an assembly of analog or digital electronic components and may be configured to execute software, which may include an operating system and one or more applications, as part of performing the functions described herein with respect to, e.g., the processing circuitry 110 of FIG. 1. The processing circuitry 210 may receive and further process physiological signals received from the front-end processing circuitry 216. For example, the processing circuitry 210 may determine one or more physiological parameter values based on the received physiological signals. For example, the processing circuitry 210 may compute one or more of blood flow metrics and/or diagnostic metrics from the LSI signal.

The processing circuitry 210 may perform any suitable signal processing of a signal, such as any suitable band-pass filtering, adaptive filtering, closed-loop filtering, any other suitable filtering, and/or any combination thereof. The processing circuitry 210 may also receive input signals from additional sources not shown. For example, the processing circuitry 210 may receive an input signal containing information about treatments provided to the subject from the user interface 230. Additional input signals may be used by the processing circuitry 210 in any of the determinations or operations it performs in accordance with the back-end processing circuitry 214 or the regional oximetry device 200.

The processing circuitry 210 is an example of the processing circuitry 110 and is configured to perform the techniques of this disclosure. For example, the processing circuitry 210 is configured to receive signals indicative of the speckle contrast from patient tissue and determine blood flow metrics or other values indicative of perfusion and vascular function.

The memory 220 may include any suitable computer-readable media capable of storing information that can be interpreted by the processing circuitry 210. In some examples, the memory 220 may store light source and detection functions, signal processing instructions, LSI signal processing instructions, blood flow metric calculation instructions, generated patient data, and the like. The back-end processing circuitry 214 may be communicatively coupled with the user interface 230 and the communication interface 290.

The user interface 230 may include the input device 234, the display 232, and the speaker 236 in some examples. The user interface 230 is an example of user interface 130 shown in FIG. 1, and the display 232 is an example of the display 132 shown in FIG. 1. The user interface 230 may include, for example, any suitable device such as one or more medical devices (e.g., a medical monitor that displays various physiological parameters, a medical alarm, or any other suitable medical device that either displays physiological parameters or uses the output of the back-end processing 214 as an input), one or more display devices (e.g., monitor, personal digital assistant (PDA), mobile phone, tablet computer, clinician workstation, any other suitable display device, or any combination thereof), one or more audio devices, one or more memory devices, one or more printing devices, any other suitable output device, or any combination thereof.

The input device 234 may include one or more of any type of user input device such as a keyboard, a mouse, a touch screen, buttons, switches, a microphone, a joy stick, a touch pad, or any other suitable input device or combination of input devices. In other examples, the input device 234 may be a pressure-sensitive or presence-sensitive display that is included as part of the display 232. The input device 234 may also receive inputs to select a model number of the sensing device 250. In some examples, the processing circuitry 210 may determine the type of presentation for the display 232 based on user inputs received by the input device 234. For example, the processing circuitry 210 may be configured to present, via the display 232, a graphical user interface.

The communication interface 290 may enable the LSI device 200 to exchange information with other external or implanted devices. The communication interface 290 may include any suitable hardware, software, or both, which may allow the LSI device 200 to communicate with electronic circuitry, a device, a network, a server or other workstations, a display, or any combination thereof.

The components of the LSI device 200 that are shown and described as separate components are shown and described as such for illustrative purposes only. In some examples the functionality of some of the components may be combined in a single component. For example, the functionality of the front end processing circuitry 216 and the back-end processing circuitry 214 may be combined in a single processor system. Additionally, in some examples the functionality of some of the components of the blood flow detection device 200 shown and described herein may be divided over multiple components. For example, some or all of the functionality of the control circuitry 245 may be performed in the front end processing circuitry 216, in the back-end processing circuitry 214, or both. In other examples, the functionality of one or more of the components may be performed in a different order or may not be required. In some examples, all of the components of the blood flow detection device 200 can be realized in processor circuitry. In one example, the LSI device 200 includes the control circuitry 245 that includes all functionality described herein with respect to the front end processing circuitry 216 and the back end processing circuitry 214.

Although transmission-based laser speckle imaging is generally described herein and, in many cases, may provide appropriate blood flow readings within a volume of tissue, reflectance-based laser speckle imaging within a region can also offer valuable blood flow information. Reflectance-based laser speckle imaging, which still provides both blood flow and waveform characteristics, may be employed by a system, such as the device 100 or device 200, when the volume of tissue is too thick to adequately pass light through. In this manner, device 100, device 200, or another device may obtain LSI signals from reflectance-based sensor configurations in some examples and generate blood flow metrics as described herein.

Figure 3:
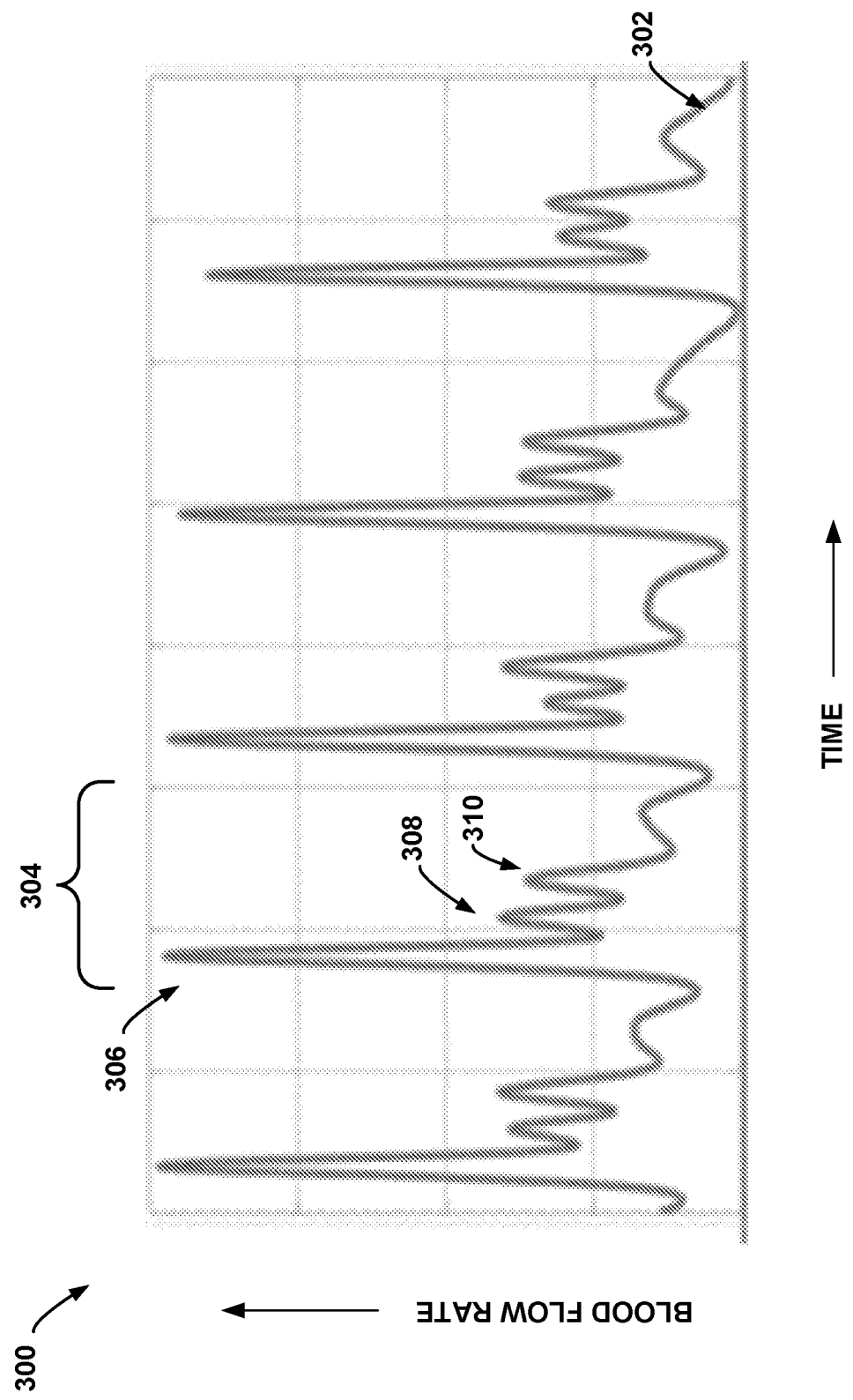
FIG. 3 illustrates an example waveform of blood flow detected using laser speckle imaging techniques.

FIG. 3 illustrates an example LSI signal 302 representative of blood flow detected using LSI techniques. As shown in the example of FIG. 3, the graph 300 includes the LSI signal 302 that is generated from the detected scattered light through a sample tissue. As described in U.S. Patent Application Publication No. 2013/0204112 by White et al. and entitled "Perfusion Assessment Using Transmission Laser Speckle Imaging," the entire contents of which are incorporated by reference herein, transmission LSI can be used to measure blood flow. This transmission LSI can be of practical use in a medical setting. As stated above, LSI measures motion of light-scattering objects, and the resulting data can be interpreted to quantify blood flow. One ability conferred by transmission LSI is the ability to longitudinally record blood flow as a function of time, such as in the LSI signal. In this manner, the processing circuitry 110 (FIG. 1) of the blood flow detection device 100 or another device can accurately detect and record minute alterations in blood flow that accompany, among other factors, heartbeat or cardiac cycle of the subject. When this data is analyzed over time, as presented in FIG. 3, each change in blood flow due to the pressure wave from heart contraction is generally referred to as a pulse waveform 304.

Blood volume changes determined from PPG data, for example, is distinct from analysis of LSI data. As such, analysis of LSI data, for example as it pertains to the pulsatile signals derived from pulsatile blood flow, has a different meaning as compared to similar analyses performed on PPG data. Not all LSI signals will be pulsatile or oscillatory, such as during surgeries requiring a heart-lung machine because such devices remove the pulsatile component of blood flow. However, these type of situations also reduce or eliminate proper blood flow monitoring using PPG techniques.

LSI signals acquired using transmission LSI may be analyzed in a plurality of manners. One non-limiting example provided herein pertains to analysis of one or more pulse waveforms derived using transmission LSI, such as shown in the LSI signal 302. These examples are not meant to be all-inclusive and are included for the purpose of illustration only and not restriction.

The LSI signal 302 may include features or characteristics that are representative of the manner in which blood flows through the vasculature. For example, each of the pulse waveforms 304 includes one or more different peaks, such as the peak 306, the peak 308, and the peak 310. Such a waveform with three peaks may be referred to as a triphasic waveform. Waveforms with two peaks may be referred to as biphasic waveforms and waveforms with one peak may be referred to as monophasic waveforms. The presence, amplitude, slopes, or other characteristics of the peaks within a waveform may be used to determine a waveform metric that categorizes the waveform. Such categories may indicate the magnitude of functional quality and/or degradation of the waveform for moving blood through the vasculature. In addition, the flow of the waveform may correspond to the flow measured during a period of time that covers a portion or all of waveform 304, such as the flow corresponding to the peak 306 (e.g., the highest peak or first peak in time), a different peak, multiple peaks, instantaneous flow rate corresponding to any one or more peaks or portions of the waveform 304, or the area under the curve of the waveform 304 for any portion of waveform 304. In this manner, a system may determine the flow for each waveform (e.g., the waveform 304) based on the diastolic flow portion, the systolic flow portion, the mean flow, or any other flow determinations. The system may determine the flow value for the waveform 304 as the mean or median flow determined over a portion or all of one or more waveforms such as the waveform 304.

Pulse waveform analysis performed by the processing circuitry 110 (or other processing circuitry) on transmission LSI data such as the LSI signal 302 may include characteristics such as measurement of the time delay between repeating features, such as: pulse waveform peak to pulse waveform peak, pulse waveform trough to pulse waveform trough, pulse waveform systolic peak to pulse waveform diastolic foot, pulse waveform dicrotic notch to pulse waveform dicrotic notch, pulse waveform systolic peak to pulse waveform dicrotic notch, pulse waveform diastolic foot to pulse waveform dicrotic notch, pulse waveform post-systolic oscillation to pulse waveform post-systolic oscillation, and/or pulse width half max. The processing circuitry 110 can use any of these characteristics or combinations thereof to generate a blood flow metric based on the LSI signal 302.

In some examples, within a single pulse waveform (e.g., the waveform 304) derived from the LSI signal 302, the processing circuitry 110 can determination one or more of the following: pulse waveform amplitude (peak to trough), pulse waveform peak to pulse waveform dicrotic notch amplitude, pulse waveform peak to pulse waveform secondary oscillation amplitude, pulse waveform width measured at any height (including the dicrotic notch and at half the peak to trough amplitude), area under the pulse waveform, pulse waveform systolic area, pulse waveform diastolic area, first derivative of the pulse waveform systolic slope, second derivative of the pulse waveform systolic slope, third derivative of the pulse waveform systolic slope, first derivative of the pulse waveform diastolic slope, second derivative of the pulse waveform diastolic slope, third derivative of the pulse waveform diastolic slope, pulse waveform linear regression slope, and/or alternations in the prevalence of pulse waveform features (for example, the dicrotic notch or post-systolic oscillations) due to physiological changes. The processing circuitry 110 can use any of these characteristics alone or in combination with any other characteristics of the LSI signal 302 to determine (e.g., analyze) the waveform metric, and eventually the blood flow metric, based on signal 302.

With more than one pulse waveform derived from the LSI signal 302, the processing circuitry can determine waveform to waveform variability, such as, but not limited to, one or more of: systolic peak variability, diastolic peak variability, average flow variability, amplitude variability, width variability, slope variability, and all measures of variability between parameters calculated using single waveform as mentioned in the previous paragraph. The processing circuitry 110 can use any of these characteristics alone or in combination with other characteristics herein to determine (e.g., analyze) the LSI signal 302 to determine the waveform metric, and eventually the blood flow metric.

In some examples, analysis of the LSI signal 302 for determining a blood flow metric (by the processing circuitry 110) may include performing frequency decomposition to provide additional or standalone hemodynamic information of clinical value. Frequency analysis of these data may provide structural details of the collected waveform or waveforms. This structure of the waveforms is affected by numerous physiological processes such as blood flow rate, vascular tone, blood pressure, cardiac output, degree of atherosclerosis, and others. As such, the frequency decomposition of the transmission LSI waveforms contain information that enables quantification of these states or processes, such as for blood flow metric and/or diagnostic purposes. The processing circuitry 110 can analyze the frequency domain information includes by at least, for example, using a wavelet or Fourier transforms to transform time-domain data into the frequency domain, followed by quantification of the magnitude of frequencies either alone or related to one or more other frequencies. In this manner, the processing circuitry 110 may determine power spectrum features at one or more frequencies and determine the waveform metrics, and eventually, the blood flow metric. In some examples, processing circuitry 110 may be configured to determine blood flow metrics from one or more elements of the waveform metric with or without blood flow values.

The techniques implemented by the processing circuitry 110 to determine flow, waveform metrics (and as a result, blood flow metrics), for example, can also be applied to multiple tissue locations, such as measuring multiple digits simultaneously. Resulting measurements from each location may provide clinical information which provides insight about the physiological processes within or state of a particular anatomical site. This information may provide clinical value alone or when compared qualitatively or quantitatively to other sites. For example, different parts of the foot are perfused predominantly from varying arteries in the leg, often referred to as angiosomes. Transmission LSI data analysis from different sites (different digits, for example) may provide clinical information specific to the artery or arteries responsible for perfusing that particular angiosome. This site-specific information may aid in diagnosis, prognosis, or monitoring of vascular disease.

Transmission LSI can additionally benefit from its ability to adopt data processing algorithms previously used for reflection LSI. For example, this includes the computation of speckle flow index (SFI) from collected transmission LSI data as follows:

$$SFI = 1/(2TK^2), \quad (3)$$

where T is the exposure time of the photodetector being used and K is the speckle contrast, computed spatially or over time.

An additional data acquisition and analysis technique used in traditional reflection LSI but which can also be applied by the processing circuitry 110 in transmission LSI is multiple exposure LSI. Multiple exposure LSI extend the range of blood flow rates over which transmission LSI is sensitive. The processing circuitry 110 can use any of these techniques to generate the LSI signal 302, or other signals, from which a system may determine one or more characteristics for generating a blood flow metric for tissue.

Figure 4:
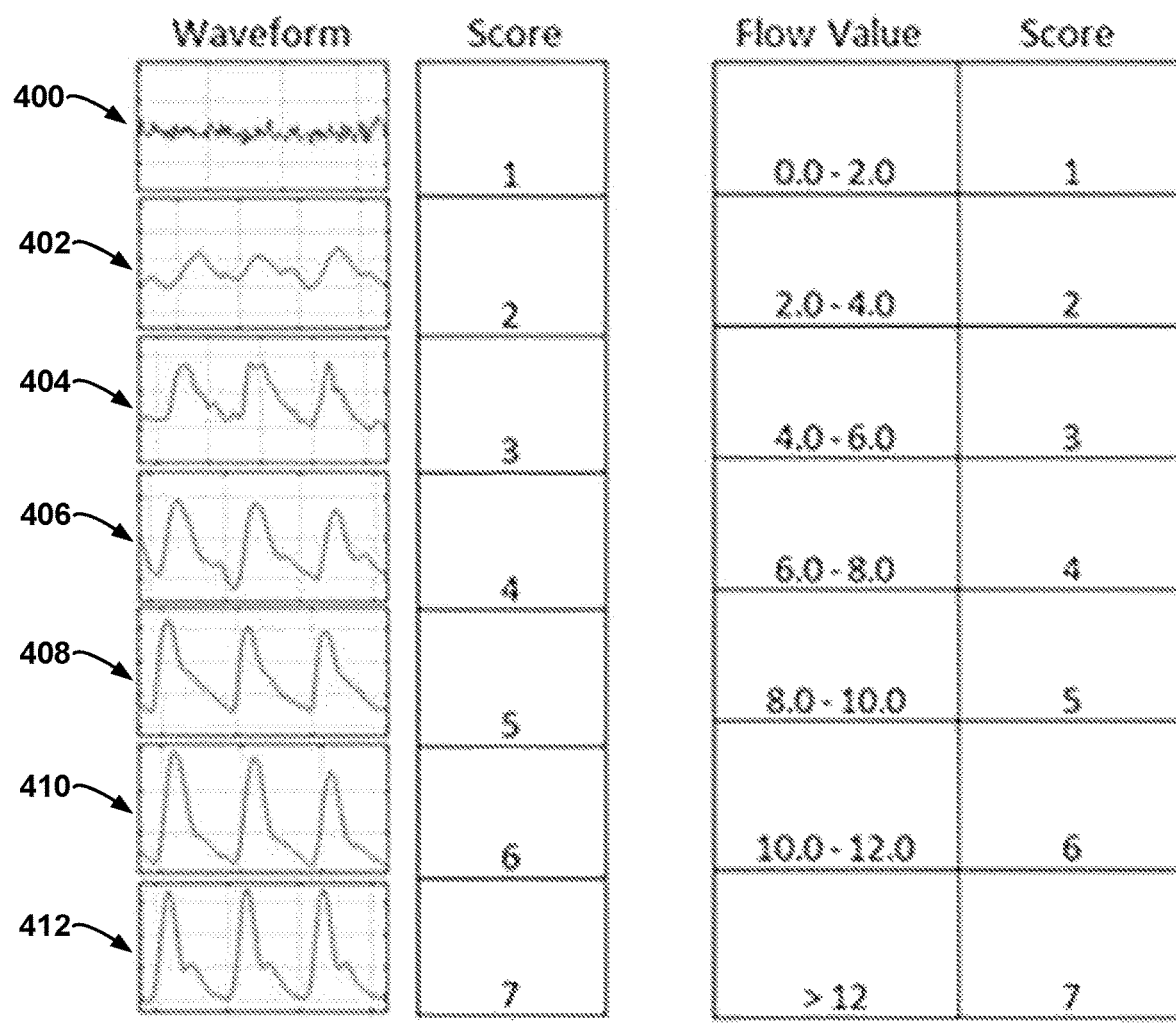
FIG. 4 is a table illustrating example waveforms and blood flow values that correspond to various blood flow states for a patient.

FIG. 4 is a table illustrating example waveforms and blood flow values that correspond to various blood flow states for a patient. This tape may be a representation of an example data structure stored by the memory and referenced by the processing circuitry to determine a score as described herein. As shown in the example of FIG. 4, various waveform shapes and flow values correspond to respective scores. Lower scores indicate greater degradation in blood flow, such that higher scores may be reflective of normal blood flow for a generally healthy subject.

For example, the waveform 400 indicates relatively minimal pulsatile structure which indicates low vascular function. Conversely, the waveform 412 indicates relatively healthy pulsatile structure indicating normal or healthy vascular function. Each of the waveforms 400, 402, 404, 406, 408, 410, and 412 represent increasing levels of vascular function with corresponding higher scores. As can be seen in the waveforms, in some cases, lower vascular function corresponds to reduce number of peaks in each pulse waveform and/or lower flow values. The flow values are shown as a normalized value without units, but any flow values can be categorized into different levels for different respective scores.

Although both the flow values and waveform shapes are categorized into seven different metric values in the example of FIG. 4, fewer or greater number of categories may be used by the processing circuitry 110 in other examples to generate outputs via user interface 130 or user interface 230. Moreover, the flow values and waveform shape metrics may have different number of categories in other examples. As described herein, the processing circuitry 110 can determine the flow values from some or all of the waveform as an instantaneous flow value or an area under the curve of the waveform that corresponds to the appropriate portion of the waveform, or combinations thereof, as some examples. The processing circuitry 110 can determine the waveform shape based on, for example, by the number of peaks in each pulse waveform, inter-peak intervals, comparison to waveform templates, or any of the other techniques described herein.

Figure 5:
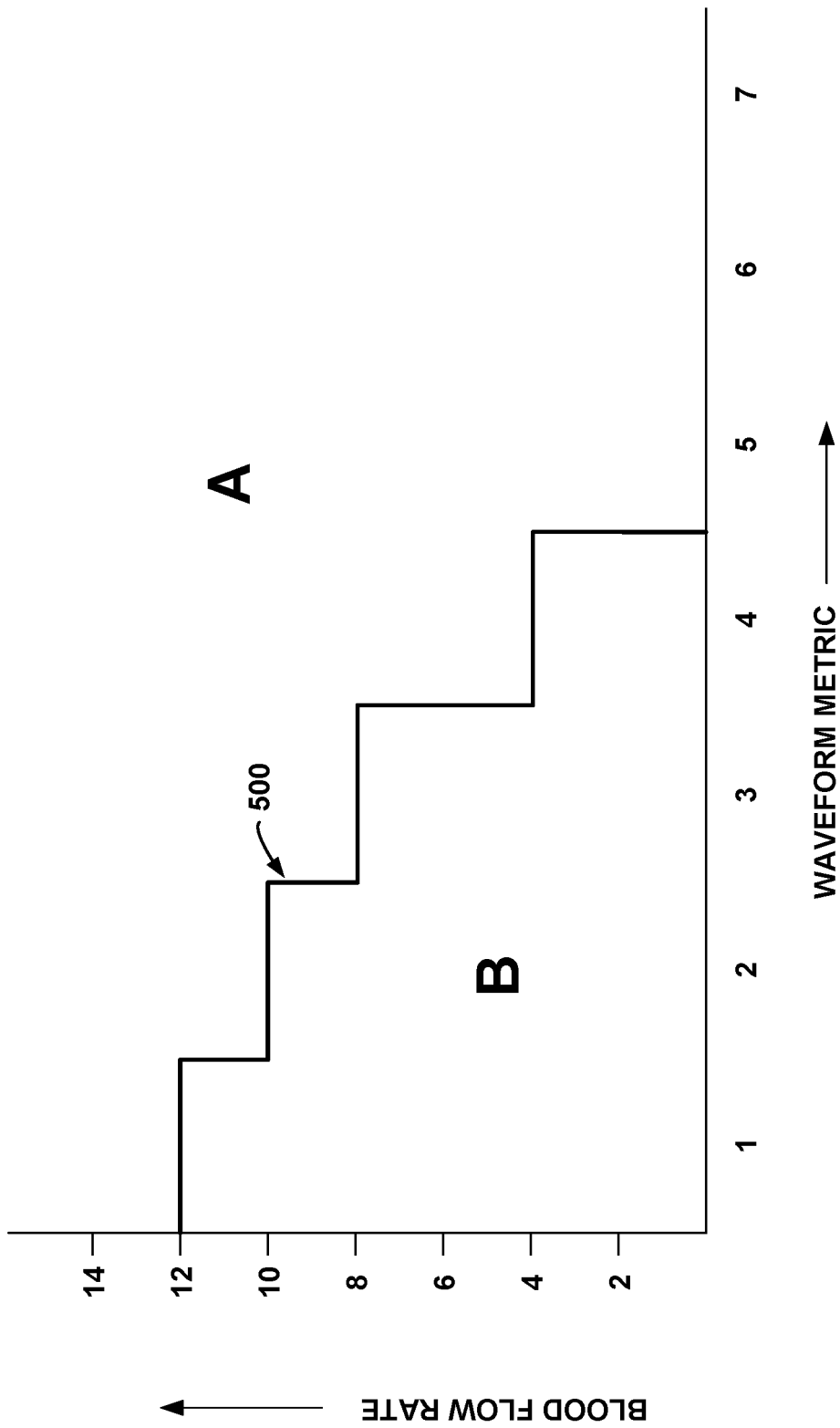
FIG. 5 is a graph illustrating example blood flow states determined from example blood flow rates and waveform metrics.

FIG. 5 is a graph illustrating example blood flow states determined from example blood flow rates and waveform metrics. As shown in the example of FIG. 5, the processing circuitry 110 can apply scores from the blood flow rate, or flow, and the waveform metric to the chart of FIG. 5 to determine a diagnostic metric, which can be output to a clinician via user interface 130 or user interface 230. In some examples, the total score of the flow and the waveform metric may be provided by the processing circuitry 110 as the blood flow metric. This blood flow metric may provide insight as to the overall vascular function of the tissue and/or subject.

In some examples, the blood flow metric, or the components from which the blood flow metric are generated by the processing circuitry 110, are categorized in order to determine a diagnostic metric. For example, the system may apply the blood flow and waveform metric to the graph (or lookup table) of FIG. 5. If the blood flow and waveform metric values fall within region A, then the processing circuitry 110 may generate a diagnostic metric that indicates a healthy vascular function. Conversely, if the blood flow value and waveform metric values fall within region B, then the processing circuitry 110 may generate a diagnostic metric that indicates a compromised vascular function, such as associated with peripheral vascular disease (PVD) or peripheral arterial disease (PAD). In this manner, a threshold 500 may separate lower blood flow metrics from higher blood flow metrics in a stepwise manner. The threshold 500 may be predetermined or determined based on the specific patient, a population of patients, or any other data and stored in memory. In other examples, threshold 500 may be equal to a single blood flow metric. In some examples, the processing circuitry 110 may employ multiple thresholds to indicate different risk levels for a certain condition, such as a low risk level, a medium risk level, and a high risk level for PVD.

Example fields of medicine where the types of analyses described above may be useful include depth of anesthesia monitoring, peripheral vascular disease diagnosis, prognosis, and monitoring, early hypovolemic shock detection, sleep apnea detection, monitoring of diabetes progression, exercise monitoring, monitoring of vascular surgical procedures, assessment of dialysis fistulas, dialysis monitoring, assessment of endothelial function, cyanide poisoning monitoring, noninvasive blood pressure measurements, heart attack, and the like. As previously mentioned, since transmission LSI has the ability to measure blood flow, the actual list of potential applications may include other types of monitoring or condition determination not specifically mentioned herein. The aforementioned topics have been described to highlight topics of potential interest and this list is not intended to preclude use in applications not mentioned.

A detailed example of the methodology and algorithm used for diagnosis and/or monitoring of specific vascular disease state (peripheral vascular disease) is presented in the example below.

Peripheral vascular disease (PVD/PAD) is a relatively common disease affecting approximately 12 million people in the United States. The ankle-brachial index (ABI) is the a initial screening test that can be used to diagnose and grade the PVD. It is also used to determine prognosis regarding limb salvation, wound healing, and future cardiovascular related morbidity.

ABI is calculated by measuring the average systolic blood pressure in the legs (at the ankle) and arms (at the forearm), and comparing these two values. The result is a ratio of ankle systolic blood pressure to the brachial systolic blood pressure. This value is typically one or less, and a diagnosis of PVD is given for an ABI less than or equal to 0.9. PVD is graded mild to moderate if the ABI falls between 0.4 and 0.9, and ABI less than 0.4 corresponds to severe PVD. ABI above 1.3 is indicative of non-compressible vessels. Because the ABI is performed as a comparative ratio instead of an absolute value, it is a normalized measurement. This accounts for and eliminates effects of natural variation in blood pressure due to daily factors such as time of day, diet, stress, exercise, alcohol intake, etc.

Despite its ubiquity, ABI can have several limitations. For example, the ABI may be unreliable when patients have arterial calcification, renal failure, or are heavy smokers. As another example, the ABI can be insensitive to mild peripheral arterial disease. As another example, the ABI may depend heavily on the individual performing the measurement, and requires skilled operators for accurate results. ABI can also take significant time to perform, e.g., approximately 15 minutes.

An alternative to diagnosing PVD with normalized ratio of measured blood pressures is to measure blood flow speed in the peripheral digits (fingers and/or toes) directly using transmission laser speckle analysis (e.g., using the LSI signal described herein), which may be followed by performing of either a comparative analysis such as a ratio of blood flow speed in the finger and toe, or an absolute analysis of the flow rate and/or waveform from the finger or toe. A comparative calculation between finger and toe may normalize the laser speckle measurement, maintaining an element in the ABI's diagnostic potential.

The laser speckle-based techniques described herein can offer several advantages over the ABI. For example, the laser speckle measurement does not require an arm cuff occlusion, thus avoiding discomfort to the patient. The laser speckle-based techniques can also be used for patients with calcified, incompressible arteries and for which ABI not be usable for diagnosis. However, blood flow speed can be quantified in these patients and used to make a diagnostic measurement. As another example, the transmission laser speckle analysis system can be constructed into a simple finger clip probe (or another relatively small form factor) and automated, which can help remove variability in outputs between operators. A simple clip design may also eliminates the need for skill and training which is required for performing the ABI.

Figure 6:
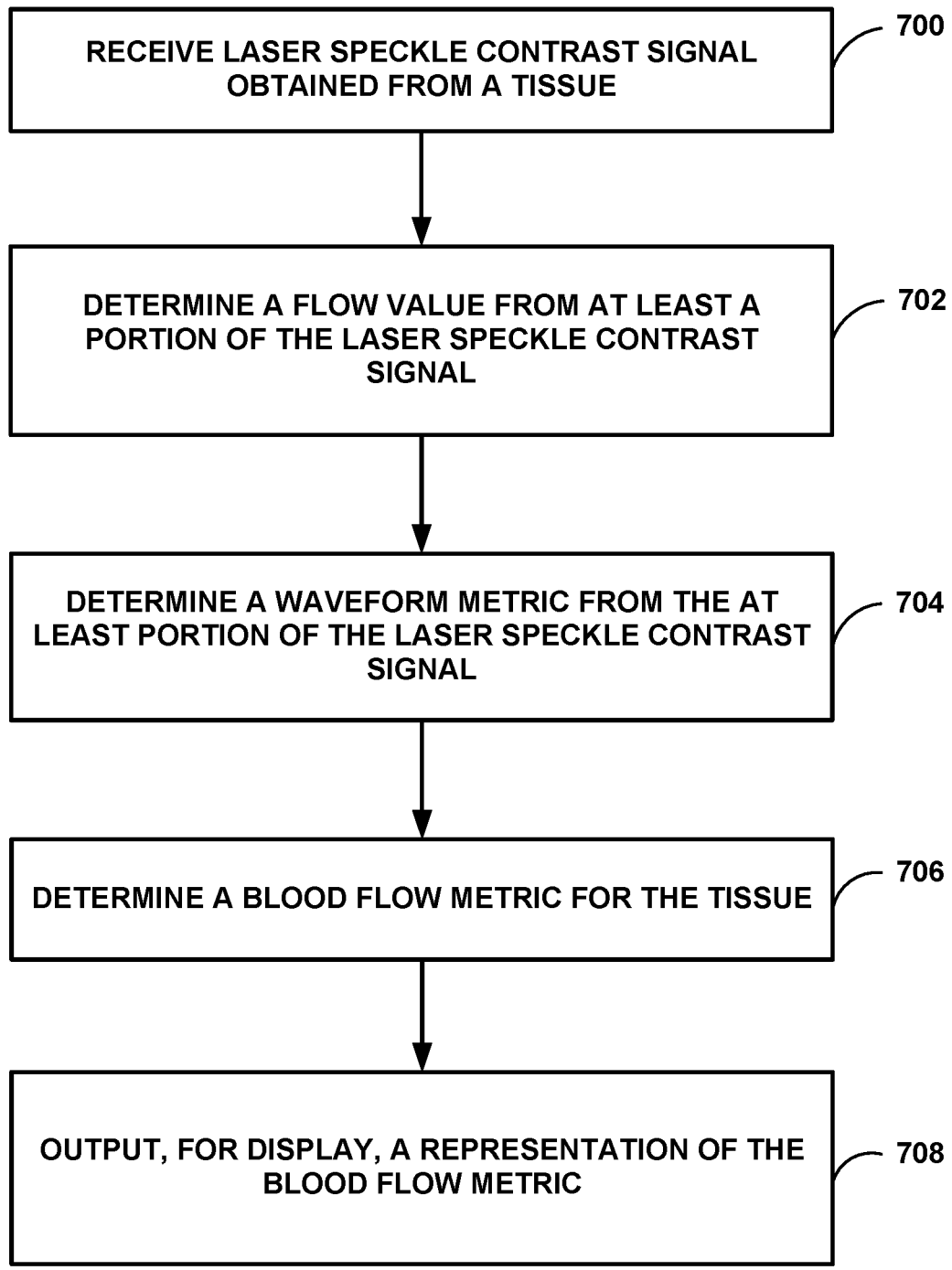
FIG. 6 is a flow diagram illustrating example techniques for determining a blood flow state for a patient using a waveform determined using laser speckle imaging techniques.

FIG. 6 is a flow diagram illustrating example techniques for determining a blood flow state for a patient using a waveform determined using LSI techniques. Although FIG. 6 is described with respect to the processing circuitry 110 of the blood flow detection device 100 (FIG. 1), in other examples, the processing circuitry 210, 214, and/or 216 (FIG. 2), or other processing circuitry, alone or in combination with the processing circuitry 110, may perform any part of the techniques of FIG. 6.

In the example of FIG. 6, the processing circuitry 110 receives a laser speckle contrast signal obtained from tissue of a subject (700). In some examples, the processing circuitry 110 may control the light source 142 to deliver light to the tissue of interest and the light sensor 152 to detect the scattered light. The processing circuitry 110 may receive the LSI signal from the light detection circuitry 150 or generate the LSI signal from a raw signal received from the light detection circuitry 150.

The processing circuitry 110 then determines a flow value from at least a portion of the laser speckle contrast signal (702) and determines a waveform metric from the at least portion of the laser speckle contrast signal (704). The processing circuitry 110 the determines a blood flow metric for the tissue based on the flow value and the waveform metric (706). The processing circuitry 110 then outputs, for display, a representation of the blood flow metric (708). In some examples, the processing circuitry 110 may also, or alternatively, determine a diagnostic metric based on the blood flow metric to indicate the probability or likelihood that the patient has a certain condition, such as PVD or PAD.

Although the example of FIG. 6 is described as including determining a flow value and waveform metric from the LSI signal to determine the blood flow metric, the processing circuitry 110 may determine the blood flow metric from other characteristics of the LSI signal in other examples. For example, the processing circuitry 110 may determine the blood flow metric based on a power spectrum of one or more frequencies and/or another characteristic described herein.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

The techniques described in this disclosure, including those attributed to devices 100 and 200 and any other processing circuitry or electrical circuitry, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

As used herein, the term "circuitry" refers to an ASIC, an electronic circuit, a processor (shared, dedicated, or group) and memory that execute one or more software or firmware programs, a combinational logic circuit, or other suitable components that provide the described functionality. The term "processing circuitry" refers one or more processors distributed across one or more devices. For example, "processing circuitry" can include a single processor or multiple processors on a device. "Processing circuitry" can also include processors on multiple devices, wherein the operations described herein may be distributed across the processors and devices.

Such hardware, software, firmware may be implemented within the same device or within separate devices to support the various operations and functions described in this disclosure. For example, any of the techniques or processes described herein may be performed within one device or at least partially distributed amongst two or more devices. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache). Elements of devices and circuitry described herein, including, but not limited to, devices 100 and 200 may be programmed with various forms of software. The one or more processors may be implemented at least in part as, or include, one or more executable applications, application modules, libraries, classes, methods, objects, routines, subroutines, firmware, and/or embedded code, for example.

Various examples of the disclosure have been described. Any combination of the described systems, operations, or functions is contemplated. These and other examples are within the scope of the following claims.

What is claimed is:

1. A system comprising:
light drive circuitry configured to cause a coherent light source to emit light of a single wavelength;
light detection circuitry configured to generate a signal indicative of detected light;
processing circuitry configured to:
control the light drive circuitry to cause the coherent light source to emit the light of the single wavelength;
receive, from the light detection circuitry, the signal indicative of the detected light scattered from the light of the single wavelength;
generate a laser speckle contrast signal based on the signal indicative of the detected light, the detected light scattered by tissue of a subject and from the coherent light source that emitted the light of the single wavelength;
determine, from the laser speckle contrast signal, a flow value;
determine, from the laser speckle contrast signal, a waveform metric;
determine, based on both the flow value and the waveform metric, a blood flow metric for the tissue; and
output, for display at a display device, a representation of the blood flow metric.

2. The system of claim 1, wherein the processing circuitry is configured to determine the waveform metric by at least determining the waveform metric based on the laser speckle contrast signal comprising at least one of a triphasic waveform, a biphasic waveform, or a monophasic waveform representative of a single cardiac cycle.

3. The system of claim 1, wherein the processing circuitry is configured to determine the waveform metric by at least:
comparing a waveform shape of the laser speckle contrast signal to a plurality of different waveform templates; and
selecting the waveform metric corresponding to one waveform template of the plurality of different waveform templates that best fits the waveform shape.

4. The system of claim 1, wherein the processing circuitry is configured to determine the blood flow metric based on a total score of the flow value and the waveform metric.

5. The system of claim 1, wherein the processing circuitry is configured to determine the blood flow metric from a lookup table defining a relationship between the flow value and the waveform metric.

6. The system of claim 1, wherein the processing circuitry is configured to:
determine the flow value by at least determining an average flow of a plurality of waveforms of the laser speckle contrast signal; and
determine the waveform metric by at least determining an average slope of the plurality of waveforms of the laser speckle contrast signal.

7. The system of claim 1, wherein the processing circuitry is configured to determine a peripheral vascular disease metric based on the blood flow metric for the tissue.

8. The system of claim 1, wherein the tissue comprises a digit of the subject.

9. The system of claim 1, further comprising the display device configured to present the representation of the blood flow metric.

10. The system of claim 1, further comprising:
the coherent light source; and
a light detector configured to detect light scattered by the tissue from the coherent light source and generate the signal indicative of the detected light.

11. A method comprising:
controlling, by processing circuitry, light drive circuitry configured to cause a coherent light source to emit light of a single wavelength;
generating, by light detection circuitry, a signal indicative of detected light scattered from the light of the single wavelength;
receiving, by the processing circuitry and from the light detection circuitry, the signal indicative of detected light;
generating, by the processing circuitry, a laser speckle contrast signal based on a the signal indicative of the detected light, the detected light scattered by tissue of a subject and from the coherent light source that emitted the light of the single wavelength;
determining, by the processing circuitry and from the laser speckle contrast signal, a flow value;
determining, by the processing circuitry and from the laser speckle contrast signal, a waveform metric;
determining, by the processing circuitry and based on both the flow value and the waveform metric, a blood flow metric for the tissue; and
outputting, by the processing circuitry and for display at a display device, a representation of the blood flow metric.

12. The method of claim 11, wherein determining the waveform metric comprises determining the waveform metric based on the laser speckle contrast signal comprising one of a triphasic waveform, a biphasic waveform, or a monophasic waveform representative of a single cardiac cycle.

13. The method of claim 11, wherein determining the waveform metric comprises:
comparing a waveform shape of the laser speckle contrast signal to a plurality of different waveform templates; and
selecting the waveform metric corresponding to one waveform template of the plurality of different waveform templates that best fits the waveform shape.

14. The method of claim 11, wherein determining the blood flow metric comprises determining the blood flow metric based on a total score of the flow value and the waveform metric.

15. The method of claim 11, wherein determining the blood flow metric comprises determining the blood flow metric from a lookup table defining a relationship between the flow value and the waveform metric.

16. The method of claim 11, wherein:
determining the flow value comprises calculating an average flow of a plurality of waveforms of the laser speckle contrast signal; and
determining the waveform metric comprises calculating an average slope of the plurality of waveforms of the laser speckle contrast signal.

17. The method of claim 11, further comprising determining a peripheral vascular disease metric based on the blood flow metric for the tissue.

18. The method of claim 11, wherein the tissue comprises a digit of a subject, and wherein the method further comprises:
delivering, via the coherent light source, the coherent light to the tissue of the digit;
detecting, via a light detector, the light scattered by the tissue of the digit from the coherent light source; and
generating, via the light detector and by the light detection circuitry, the signal indicative of the detected light.

19. The method of claim 11, further comprising presenting, via the display device, the representation of the blood flow metric.

20. A non-transitory computer-readable medium comprising instructions that, when executed, causes processing circuitry to:
control light drive circuitry to cause a coherent light source to emit light of a single wavelength;
receive, from light detection circuitry, a signal indicative of detected light, wherein the light detection circuitry is configured to generate the signal indicative of the detected light;
generate a laser speckle contrast signal based on the signal indicative of the detected light, the detected light scattered by tissue of a subject and from the coherent light source that emitted the light of the single wavelength;
determine, from the laser speckle contrast signal, a flow value;
determine, from the laser speckle contrast signal, a waveform metric;
determine, based on both the flow value and the waveform metric, a blood flow metric for the tissue; and
output, for display at a display device, a representation of the blood flow metric.

* * * * *